United States Patent [19]

Soma et al.

[11] 3,951,661

[45] Apr. 20, 1976

[54] SILVER HALIDE EMULSION CONTAINING AN ARYLPHOSPHONIUM SALT AS ANTIFOGGANT

[75] Inventors: Nobuo Soma; Isao Kawamoto, both of Hiro; Tomio Nakajima, Shin; Sadao Sugita, Hanno; Tsuneo Wada, Machida; Shizuo Saito, Hachioji; Hiroyuki Inokuma, Chofu; Koichi Horigome, Tokyo; Yukio Morifuji, Hachioji, all of Japan

[73] Assignees: Konishiroku Photo Industry Co.; Sankyo Company Limited, both of Tokyo, Japan

[22] Filed: May 24, 1974

[21] Appl. No.: 473,315

Related U.S. Application Data

[63] Continuation-in-part of Ser. No. 247,512, April 26, 1972.

[30] Foreign Application Priority Data

Apr. 30, 1971   Japan.................................. 46-28720

[52] U.S. Cl. ................................. 96/76 R; 96/87 R; 96/109

[51] Int. Cl.² ........................................... G03C 1/34
[58] Field of Search...................... 96/109, 87, 76 R

[56] References Cited
UNITED STATES PATENTS 2,238,632   4/1941   Dersch et al........................... 96/109
3,615,510   10/1971   Yudelson .............................. 96/109

Primary Examiner—Won H. Louie, Jr.
Attorney, Agent, or Firm—Haseltine, Lake & Waters

[57] ABSTRACT

Substances of the structure

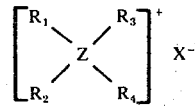

wherein Z is phosphorus, X⁻is Cl⁻, Br⁻, ClO₂⁻ or BF₄⁻, and R₁ – R₄ are alkyl or aromatic groups are excellent inhibitors of fog formation when incorporated in photographic emulsions containing silver halides.

4 Claims, No Drawings

SILVER HALIDE EMULSION CONTAINING AN ARYLPHOSPHONIUM SALT AS ANTIFOGGANT

This is a continuation-in-part of our application Ser. No. 247,512, filed Apr. 26, 1972.

This invention relates to light-sensitive silver halide photographic materials containing novel antifoggants.

Recently, the mechanical and quick treatment of light-sensitive photographic materials has advanced vigorously, and it has become an ordinary practice to treat photographic materials under such severe conditions as never imagined before. If conventional photographic materials are treated as they are, therefore, various unexpected drawbacks are brought about. For example, in case a photographic material is treated automatically and quickly by use of an automatic developing machine, fog is liable to be formed due to the composition of developer which is different from that of a conventional developer, or to a high temperature adopted in the development, whereby the resulting image is frequently deteriorated in quality. This tendency is displayed more markedly as the photographic material is made higher in speed or the development is conducted more quickly. Such fog can tentatively be inhibited by use of conventional antifoggant, but the amount of conventional antifoggant required in this case is 4 to 10 times the amount required in an ordinary case, with the result that marked desensitization is necessarily brought about. Accordingly, the use of conventional antifoggant is not practical, and it is the actual state that there is substantially no antifoggant capable of inhibiting such fog.

A principal object of the present invention is to provide a light-sensitive silver halide photographic material which can inhibit the above-mentioned fog and give excellent photographic properties even when treated under severe conditions.

As the result of extensive studies, we have found that the abovementioned object can successfully be accomplished by incorporating into at least one layer of a light-sensitive silver halide photographic material, e.g. at least one of such layers formed on a support as sub layer, inter layer, emulsion layer, protective layer, etc., a compound of the general formula,

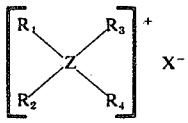

wherein Z is P; $R_1$, $R_2$, $R_3$ and $R_4$ are individually an alkyl, aryl, or aralkyl group, at least one of said $R_1$, $R_2$, $R_3$ and $R_4$ being an aryl or aralkyl group having an electron-attractive substituent; and $X^-$ is an acid anion which is selected from the group consisting of $Cl^-$, $Br^-$, $ClO_2^-$ and $BF_4^-$.

Compounds of the above-mentioned general formula can be synthesized according to such procedures as shown in the following synthesis examples:

Synthesis Example 1

Synthesis of p-nitrophenyl-di-(p-tolyl)-phenyl phosphonium iodide (the exemplified compound (1) shown later):

13.8 Grams of p-nitroaniline was dissolved at an elevated temperature in a solution comprising 30 ml. of concentrated hydrochloric acid (35%) and 20 ml. of water. This solution was poured into 170 g. of ice, and then a solution of 6.91 g. of sodium nitrite in 20 ml. of water was added to said solution. Subsequently, the mixed solution was reacted with stirring at 0° to 5°C. for 30 minutes to form a p-nitroaniline diazonium salt solution. To this solution were added a solution of 30 g. of sodium acetate in 50 ml. of water and then a solution of 29.0 g. of di-p- tolyl phenylphosphine in 40 ml. of ethyl acetate, and the mixed solution was reacted at 25°C. for 10 hours. After completion of the reaction, the aqueous layer was separated, incorporated with excess hydroiodic acid and then extracted with chloroform, and the chloroform layer was concentrated to obtain 16.7 g. of the end compound. Elementary analysis values of the thus obtained compound were as set forth in Table 1 shown later.

Synthesis Example 2

Synthesis of p-nitrobenzyl triphenylphosphonium bromide [the exemplified compound (3) shown later]:

A mixture comprising 22 g. of triphenylphosphine and 16.6 g. of p-nitrobenzyl bromide was dissolved in 200 ml. of xylene, and the resulting solution was refluxed for 26 hours to deposit a precipitate. This precipitate was recovered by filtration and then washed with 20 ml. of xylene to obtain 35.6 g. of the end compound. Elementary analysis values of the thus obtained compound were as set forth in Table 1 shown later.

Other compounds can also be synthesized according to the above-mentioned synthesis procedures. Typical examples of the thus synthesized compounds of the aforesaid general formula are enumerated in Table 1. Typical as the electron-attractive substituent in the aforesaid general formula are nitro, cyano, carbonyl, carboxyl, sulfonyl and quaternary amino groups and halogen atoms.

Table 1

| Exemplified Compound No. | Chemical Formula | Elementary Analysis | |
|---|---|---|---|
| | | Calculated | Found |
| (1) | 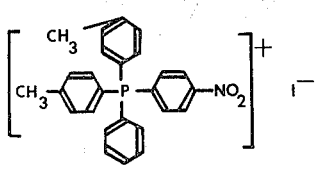 | C 57.90<br>H 4.30<br>N 2.60<br>I 23.53<br>P 5.74 | C 58.10<br>H 4.25<br>N 2.58<br>I 23.60<br>P 5.91 |

Table 1-continued

| Exemplified Compound No. | Chemical Formula | Elementary Analysis Calculated | | Found | |
|---|---|---|---|---|---|
| (2) | 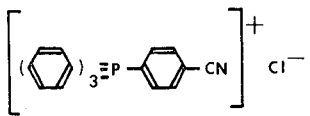 | C<br>H<br>N<br>Cl<br>P | 75.08<br>4.09<br>3.50<br>8.87<br>7.75 | C<br>H<br>N<br>Cl<br>P | 75.01<br>4.30<br>3.50<br>8.92<br>7.45 |
| (3) | 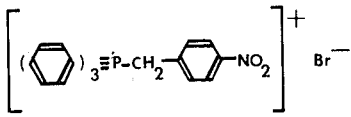 | C<br>H<br>N<br>Br<br>P | 62.77<br>4.43<br>2.93<br>16.71<br>6.48 | C<br>H<br>N<br>Br<br>P | 62.50<br>4.40<br>2.78<br>17.01<br>6.52 |
| (4) | 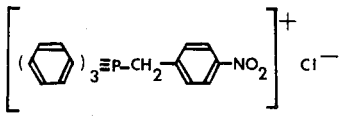 | C<br>H<br>N<br>Cl<br>P | 69.21<br>4.88<br>3.23<br>8.17<br>7.14 | C<br>H<br>N<br>Cl<br>P | 69.18<br>4.78<br>3.10<br>8.01<br>7.18 |
| (5) | 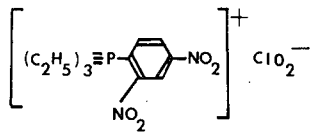 | C<br>H<br>N<br>Cl<br>P | 37.46<br>4.71<br>7.28<br>9.22<br>8.05 | C<br>H<br>N<br>Cl<br>P | 37.44<br>4.81<br>8.00<br>9.36<br>8.15 |
| (6) | 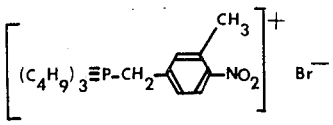 | C<br>H<br>N<br>Br<br>P | 55.55<br>8.16<br>3.24<br>18.48<br>7.16 | C<br>H<br>N<br>Br<br>P | 55.91<br>8.21<br>3.20<br>18.35<br>7.01 |
| (7) | 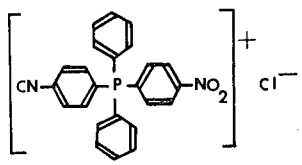 | C<br>H<br>N<br>Cl<br>P | 67.17<br>4.08<br>6.30<br>7.97<br>6.96 | C<br>H<br>N<br>Cl<br>P | 67.85<br>4.00<br>5.99<br>7.85<br>7.01 |
| (8) | 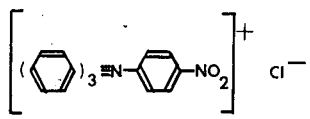 | C<br>H<br>N<br>Cl | 71.55<br>4.75<br>6.96<br>8.80 | C<br>H<br>N<br>Cl | 71.72<br>4.91<br>6.75<br>8.75 |
| (9) | 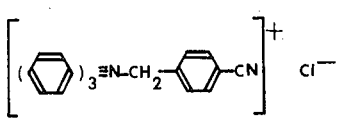 | C<br>H<br>N<br>Cl | 78.67<br>5.33<br>7.06<br>8.93 | C<br>H<br>N<br>Cl | 78.91<br>5.24<br>7.05<br>8.52 |

Table 1-continued

| Exemplified Compound No. | Chemical Formula | Elementary Analysis Calculated | | Found | |
|---|---|---|---|---|---|
| (10) | [HOH₄C₂-P(Ph)₂-C₆H₄-NO₂]⁺ Br⁻ | C<br>H<br>N<br>Br<br>P | 55.57<br>4.43<br>3.24<br>18.49<br>7.17 | C<br>H<br>N<br>Br<br>P | 55.68<br>4.61<br>3.20<br>18.51<br>7.07 |
| (11) | [C₂H₅-P(Ph)₂-CH₂-C₆H₄-COOC₂H₅]⁺ I⁻ | C<br>H<br>I<br>P | 57.13<br>5.19<br>25.15<br>6.14 | C<br>H<br>I<br>P | 57.41<br>5.30<br>24.75<br>6.34 |
| (12) | [(Ph)₃≡P-C₆H₄-N(C₂H₅)₂·HCl]⁺ Cl⁻ | C<br>H<br>N<br>Cl<br>P | 69.70<br>6.27<br>2.90<br>14.70<br>6.42 | C<br>H<br>N<br>Cl<br>P | 70.31<br>6.01<br>3.20<br>14.51<br>6.21 |
| (13) | [(Ph)₃≡P-C₆H₄-SO₂CH₃]⁺ BF₄⁻ | C<br>H<br>S<br>F<br>P | 59.54<br>4.40<br>6.36<br>15.07<br>6.14 | C<br>H<br>S<br>F<br>P | 59.76<br>4.32<br>6.70<br>15.21<br>6.01 |
| (14) | [(Ph)₃≡P-C₆H₄-COCH₃]⁺ Cl⁻ | C<br>H<br>Cl<br>P | 74.90<br>5.32<br>8.27<br>7.43 | C<br>H<br>Cl<br>P | 75.02<br>5.10<br>8.05<br>7.56 |

Table 1-continued

| Exemplified Compound No. | Chemical Formula | Elementary Analysis Calculated | | Found | |
| --- | --- | --- | --- | --- | --- |
| (15) | $[(C_6H_5)_3\equiv P-C_6H_4-Cl]^+ Cl^-$ | C | 70.42 | C | 70.67 |
| | | H | 4.68 | H | 4.73 |
| | | Cl | 17.33 | Cl | 17.12 |
| | | P | 7.57 | P | 7.48 |

These compounds of the present invention show excellent antifogging effect as compared with the conventional antifoggants and successfully inhibit the fog which is liable to be formed under severe conditions, as mentioned previously. This prominent effect is ascribable to the fact that the compounds of the present invention contain an aryl or aralkyl group having an electronattractive substituent (of course, the said aryl or aralkyl group may have other substituent). This is confirmed by the fact that a compound, which is similar in chemical structure to the compound of the aforesaid general formula but contains an aryl or aralkyl group having no electron-attractive substituent, can effectively inhibit the resulting photographic material from formation of ordinary fog but has no substantial effect on the fog formed when the photographic material is treated under severe conditions, as seen in Example 1 shown later.

In incorporating into a layer of lightsensitive silver halide photographic material, the compound of the aforesaid general formula may be dissolved in water or in a water-miscible organic solvent such as methanol, ethanol or the like, and then incorporated into a suitable layer. The amount of the compound used in the above case varies depending on the kind of silver halide, the kind of layer into which the compound is to be incorporated, the kind of the compound used, etc. Generally, however, the amount of the compound to be incorporated into an emulsion layer is desirably in the range from $10^{-2}$ to $10^{-5}$ mole per mole of the silver halide, and the amount of the compound to be incorporated into a sub layer, inter layer, protective layer, or the like is desirably in the range from $10^{-2}$ to $10^{-6}$ per $m^2$ of the photographic material, though the amount is not always limited to the above-mentioned range but can be suitably selected according to the intended application.

The silver halide emulsion used in the photographic material, into which the compound of the present invention is incorporated, may be any of emulsions of such silver halides as silver iodobromide, silver chlorobromide, silver chloroiodobromide, silver bromide and silver chloride. The said emulsion may contain, according to the prior art photography, any of various inhibitors, stabilizers, sensitizing dyes, couplers, sensitizers, hardeners, and other photographic additives. Even when made present together with such various additives, the compound of the aforesaid general formula successfully displays its effect without bringing about any detrimental interactions.

The light-sensitive silver halide photographic material thus obtained is not only inhibited from ordinary fog but is also effectively inhibited from the fog formed under severe conditions and which has never been inhibited by use of the conventional antifoggants.

Further, the compound used in the present invention has such property that it effectively inhibits the increase of fog which is considered ascribable to the by-product of a polyester support, when a polyester resin has been used as the support of a photographic material, or to catalyst residue or the like.

The present invention is illustrated in detail below and reference to examples, but it is needless to say that the scope of the invention is not limited to the examples.

EXAMPLE 1

A silver iodobromide emulsion containing 1.5 mole% of silver iodide was subjected to ordinary second ripening, and then incorporated with 4-hydroxy6-methyl-1,3,3a,7-tetrazaindene. Thereafter, the emulsion was equally divided into several portions, which were then individually incorporated with each of the compounds shown in Table 2. Further, the emulsions were individually incorporated with formalin and saponin, coated on a cellulose triacetate support and then dried to prepare test samples.

For comparison, a control sample was prepared in the same manner as above, except that there was used the compound shown below which was similar in structure to each of the compounds shown in Table 2 but had no electron-attractive substituent. Control compound:

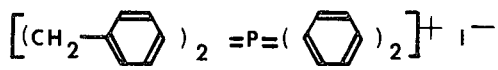

Subsequently, each sample was developed, without exposure, at 34°C. for 50 seconds by use of an automatic developing machine using a developer of the following composition (I):

Developer composition (I):
- Sodium sulfite — 70 g.
- Hydroquinone — 10 g.
- Boric anhydride — 1 g.
- Sodium carbonate (monohydrate) — 20 g.
- 1-Phenyl-3-pyrazolidone — 0.35 g.
- Sodium hydroxide — 5 g.
- 5-Methylbenzotriazole — 0.05 g.
- Potassium bromide — 5 g.
- Glutaraldehyde bisulfite — 15 g.
- Acetic acid — 8 g.
- Water to make — 1 liter The thus developed samples were individually treated with nitric acid, and the amount of reduced silver dissolved therein per 100 cm² of each sample were determined by use of a Perkin-Elmer atomic absorptiometric apparatus, Model 303, to compare the samples in degree of fog.

On the other hand, the samples were subjected to sensitometry according to JIS-K-7604 to compare them in speed.

The results obtained were as set forth in Table 2, in which the speed was represented by a relative value measured by assuming as 100 the speed of the sample (1).

Developer composition (II):
    Monomethyl-p-aminophenol sulfate        3.5 g.
    Sodium sulfite (anhydrous)              60 g.
    Hydroquinone                            9 g.
    Sodium-carbonate (monohydrate)          53 g.
    Potassium bromide                       4 g.
    Water to make                           1 liter The development was carried out without using an automatic developing machine.

Subsequently, the developed samples were measured in fog and speed. The results obtained were as set forth in Table 3, in which the speed was represented by a relative value measured by assuming as 100 the speed of the sample (13).

Table 2

| Sample No. | Compound | Amount (per Ag × 1 mole) | Fog (amount of silver per 100 cm² of sample) | Speed |
|---|---|---|---|---|
| (1) | None | — | 14.8 mg. | 100 |
| (2) | Control compound | 200 mg. | 13.7 mg. | 97 |
| (3) | " | 1,500 mg. | 5.1 mg. | 32 |
| (4) | Exemplified compound (1) | 100 mg. | 3.3 mg. | 98 |
| (5) | " | 150 mg. | 2.0 mg. | 91 |
| (6) | Exemplified compound (2) | 150 mg. | 2.9 mg. | 94 |
| (7) | Exemplified compound (5) | 175 mg. | 1.8 mg. | 88 |
| (8) | Exemplified compound (8) | 250 mg. | 3.9 mg. | 96 |
| (9) | Exemplified compound (12) | 150 mg. | 3.2 mg. | 95 |
| (10) | Exemplified compound (13) | 150 mg. | 3.0 mg. | 93 |
| (11) | Exemplified compound (14) | 200 mg. | 3.4 mg. | 97 |
| (12) | Exemplified compound (15) | 250 mg. | 3.7 mg. | 96 |

As is clear from Table 2, it is understood that the conventional compound having no electronattractive group in the molecule is required to be used in large amount in order to inhibit the fog formed when the resulting photographic material is developed by use of an automatic developing machine, and the photographic material incorporated with said compound is greatly deteriorated in speed, whereas the samples according to the present invention are successfully inhibited from said fog without being deteriorated in photographic properties.

EXAMPLE 2

A silver iodobromide emulsion containing 3 mole% of silver iodide was subjected to ordinary second ripening and then color-sensitized by addition of 3,3',8-triethylthiacarbocyanine bromide. To the thus treated emulsion were added an aqueous 1,2-benzo-5-methyl-7-hydroxy-3,4,7a-triazaindene solution, formalin and saponin. Thereafter, the emulsion was coated on a cellulose triacetate support and a polyester support to prepare samples (13) and (14), respectively.

On the other hand, the above-mentioned emulsion prior to coating on the support was incorporated with the exemplified compound (3) in a proportion of 150 mg. per mole of silver halide. Subsequently, the emulsion was coated on a polyester support and then dried to prepare a sample (15).

These samples were developed at 40°C. for 30 seconds with the aforesaid developer (I). On the other hand, the samples were incubated for 5 days in an atmosphere kept at a temperature of 55°C. and a relative humidity of 5%, and then developed at 20°C. for 4 minutes and 30 seconds with a developer (II) of the following composition:

Table 3

| Sample No. | Developed with developer (I) at 40°C for 30 sec. immediately after preparation | | Developed with developer (II) at 20°C. for 4 min. 30 sec. after incubation for 5 days | |
|---|---|---|---|---|
| | Fog | Speed | Fog | Speed |
| (13) | 0.11 | 100 | 0.23 | 100 |
| (14) | 0.42 | 107 | 0.42 | 97 |
| (15) | 0.12 | 102 | 0.23 | 101 |

From Table 3, it is understood that the compound used in the present invention displays prominent effect for inhibiting the fog derived from the polyester support as well, and successfully inhibits the fog without deteriorating the photographic properties of the photographic material incorporated therewith even when the photographic material is subjected to high temperature quick treatment and incubated in a high temperature atmosphere.

EXAMPLE 3

A silver iodobromide emulsion containing 1.5 mole% of silver iodide was subjected to ordinary second ripening and then incorporated with 4-hydroxy-6-methyl1,3-,3a,7-tetrazaindene. Further, the emulsion was incorporated with formalin, saponin, etc., and then equally divided into two portions. One emulsion was left as it was, while the other emulsion was incorporated with the exemplified compound (7) in a proportion of 140 mg. per mole of silver halide. These emulsions were individually coated on a cellulose triacetate support and then dried to prepare samples (16) and (17), respectively. The thus prepared samples were developed with the aforesaid developer (I) and then measured in fog and speed. The results obtained were as set forth in Table 4, in which the speed was represented by a relative value measured by assuming as 100 the speed of the control sample (16).

Table 4

| Sample No. | Compound | Developed immediately with developer (I) | | | | Developed with developer (I) at 36°C. for 40 sec. after incubation for 6 months | |
|---|---|---|---|---|---|---|---|
| | | Developed at 36°C. for 45 sec. | | Developed at 36°C. for 90 sec. | | | |
| | | Fog | Speed | Fog | Speed | Fog | Speed |
| (16) | None | 0.18 | 100 | 0.35 | 100 | 0.26 | 100 |
| (17) | Exemplified compound (7) | 0.12 | 100 | 0.22 | 101 | 0.20 | 100 |

As is clear from Table 4, the sample according to the present invention is successfully inhibited from fog and is not deteriorated in speed even in the case where it is developed at a high temperature and in the case where it is developed at a high temperature after incubation for a long period of time.

EXAMPLE 4

A silver iodobromide solution containing 3 mole% of silver iodide was subjected to ordinary second ripening and then incorporated with 1,2-benzo-5-methyl7-hydroxy-3,4,7a-triazaindene and 1-phenyl-5-mercaptotetrazole. Further, the emulsion was incorporated with formalin, saponin, etc., coated on a cellulose triacetate support and then dried to form an emulsion layer on the support.

On the other hand, a 5% gelatin solution was prepared as a protective layer-forming solution and equally divided into several solutions. These solutions were individually incorporated with each of the compounds shown in Table 5, coated on the aforesaid emulsion layer and then dried to prepare test samples.

In the same manner as in Example 1, the thus prepared samples were developed by use of an automatic developing machine, and measured in fog and speed. The results obtained were as set forth in Table 5.

Table 5

| Sample No. | Compound | Amount (per liter of protective layer solution) | Fog (amount of silver per 100 cm² of sample | Speed |
|---|---|---|---|---|
| (18) | None | — | 14.0 | 100 |
| (19) | Exemplified compound (3) | 200 mg. | 1.8 | 96 |
| (20) | Exemplified compound (4) | 200 mg. | 2.0 | 97 |
| (21) | Exemplified compound (6) | 200 mg. | 2.4 | 104 |
| (22) | Exemplified compound (9) | 200 mg. | 2.7 | 101 |

As is clear from Table 5, it is understood that even when incorporated into protective layers, the compounds of the aforesaid general formula display excellent antifogging effects.

What we claim is:

1. A light-sensitive silver halide photographic material which comprises a support, at least two layers on said support, one of said layers being an emulsion layer containing the silver halide and at least one of the remaining layers being a non-emulsion layer, and a fog-inhibiting substance incorporated in one of said layers, in the amount of about $10^{-2}$ to $10^{-5}$ mols per mol of silver halide when incorporated in the emulsion layer, and in the amount of about $10^{-2}$ to $10^{-6}$ mols per square meter when incorporated in a non-emulsion layer, said fog-inhibiting substance being a compound of the formula

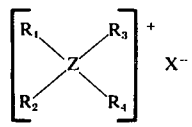

wherein
Z is phosphorus,
$X^-$ is an acidic anion, selected from the group consisting of $Cl^-$, $Br^-$, $BF_4^-$ and $ClO_2^-$, and
$R_1$, $R_2$, $R_3$, and $R_4$ may be the same or different and are selected from the grouup consisting of alkyl having 1 to 4 carbon atoms, phenyl, benzyl, tolyl, phenyl substituted with an electron-attracting group and benzyl substitued with an electron-attracting group, at least one of said $R_1$, $R_2$, $R_3$ and $R_4$ being said substituted phenyl or said substituted benzyl, wherein the electron-attracting substituent is selected from the group consisting of nitro, cyano, carbonyl, carboxyl, sulfonyl, halogen, and quaternary amino.

2. A light-sensitive silver halide photographic material according to claim 1 wherein
Z is phosphorus,
$R_1$, $R_2$ and $R_3$ are alkyl having 1 - 4 carbon atoms or phenyl, and
$R_4$ is a substituted phenyl of the formula

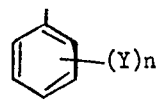

wherein Y is nitro, cyano or chloro and $n$ is 1 or 2.

3. A light-sensitive silver halide photographic material as claimed in claim 1, wherein said support is a polyester film base.

4. A light sensitive silver halide photographic material as claimed in claim 1, wherein said compound is one of p-cyanophenyl triphenylphosphonium chloride, p-nitrobenzyl triphenylphosphonium bromide, p-nitrobenzyl triphenylphosphonium chloride, 2,4-dinitrophenyl triethylphosphonium chloride, 3-methyl-4-nitrobenzyl tributylphosphonium bromide, p-nitrophenyl, p-nitrophenyl 2-hydroxyethyl diphenylphosphonium bromide, m-diethylaminophenyl triphenylphosphonium chloride hydrochloride p-cyanophenyl diphenylphosphonium chloride, p-methylsulfonylphenyl triphenylphosphonium tetrafluoroborate, p-acetylphenyl triphenylphosphonium chloride or p-chlorophenyl triphenylphosphonium chloride.

* * * * *